(12) United States Patent
Simon et al.

(10) Patent No.: US 10,918,324 B2
(45) Date of Patent: Feb. 16, 2021

(54) MULTIMODAL HEALTH ASSESSMENT WITH NEURO-OPTHALMOLOGICAL SACCADE TESTS

(71) Applicant: CERORA, INC., Bethlehem, PA (US)

(72) Inventors: Adam J. Simon, Yardley, PA (US); David M. Devilbiss, Madison, WI (US)

(73) Assignee: Cerora, Inc., Bethlehem, PA (US)

(*) Notice: Subject to any disclaimer, the term of this patent is extended or adjusted under 35 U.S.C. 154(b) by 258 days.

(21) Appl. No.: 15/315,092

(22) PCT Filed: May 29, 2015

(86) PCT No.: PCT/US2015/033294
§ 371 (c)(1),
(2) Date: Nov. 30, 2016

(87) PCT Pub. No.: WO2015/184333
PCT Pub. Date: Dec. 3, 2015

(65) Prior Publication Data
US 2017/0112427 A1    Apr. 27, 2017

Related U.S. Application Data

(60) Provisional application No. 62/005,639, filed on May 30, 2014.

(51) Int. Cl.
*A61B 5/00* (2006.01)
*A61B 5/0484* (2006.01)
(Continued)

(52) U.S. Cl.
CPC .............. *A61B 5/4064* (2013.01); *A61B 3/02* (2013.01); *A61B 5/0496* (2013.01);
(Continued)

(58) Field of Classification Search
CPC ........ A61B 5/11; A61B 5/0469; A61B 5/4064; A61B 5/04842; A61B 3/02
See application file for complete search history.

(56) References Cited

U.S. PATENT DOCUMENTS

| | | | |
|---|---|---|---|
| 7,264,595 B2 * | 9/2007 | Lamm | A61B 5/168 600/558 |
| 8,343,066 B1 * | 1/2013 | Eagleman | A61B 5/04842 600/558 |
| 2002/0099305 A1 | 7/2002 | Fukushima et al. | |
| 2005/0024588 A1 * | 2/2005 | Lamm | A61B 5/168 351/246 |

(Continued)

FOREIGN PATENT DOCUMENTS

WO    2015184333    12/2015

OTHER PUBLICATIONS

Saslow, Effects of Components of Displacement-Step Stimuli Upon Latency for Saccadic Eye Movement, Aug. 1967, Journal of the Optical Society of America, vol. 57, No. 8, p. 1024-1029.*

(Continued)

*Primary Examiner* — Daniel L Cerioni
*Assistant Examiner* — Raymond P Dulman
(74) *Attorney, Agent, or Firm* — Culhane Meadows PLLC; Michael P. Dunnam

(57) ABSTRACT

A system and method for assessing brain health includes presenting a saccade test to a subject and capturing biological sensor data of the subject in response to the saccade test using a plurality of biological sensors. Saccade cards are employed to measure the brain health of a subject through collection of eye tracking data, for example. Saccade cards using a variety of design elements besides numbers are used for collection of the eye tracking data and other biological data. The captured biological data is used to create a multi-variate signature of the brain health condition of the subject.

15 Claims, 18 Drawing Sheets

(51) Int. Cl.
*A61B 5/0496* (2006.01)
*A61B 5/11* (2006.01)
*A61B 3/02* (2006.01)

(52) U.S. Cl.
CPC ........ *A61B 5/04842* (2013.01); *A61B 5/1103* (2013.01); *A61B 5/1128* (2013.01)

(56) References Cited

U.S. PATENT DOCUMENTS

| | | | | |
|---|---|---|---|---|
| 2008/0004544 | A1* | 1/2008 | Caplygin | A61B 5/168 600/558 |
| 2008/0108883 | A1* | 5/2008 | Scott | A61B 5/1121 600/300 |
| 2008/0188777 | A1* | 8/2008 | Bedziouk | A61B 3/113 600/595 |
| 2008/0255949 | A1* | 10/2008 | Genco | A61B 5/0205 705/14.4 |
| 2009/0164132 | A1* | 6/2009 | Jung | G16B 45/00 702/19 |
| 2012/0059282 | A1 | 3/2012 | Agichtein et al. | |
| 2013/0012832 | A1* | 1/2013 | Zelinsky | A61B 5/0042 600/558 |
| 2013/0053720 | A1* | 2/2013 | Sakaguchi | A61B 5/0484 600/544 |
| 2013/0278899 | A1 | 10/2013 | Waldorf et al. | |
| 2015/0305965 | A1* | 10/2015 | Devick | G09B 5/02 351/203 |

OTHER PUBLICATIONS

Inhoff, et al. Temporal dynamics of eye-voice span and eye movement control during oral reading, Jan. 2011, Journal of Cognitive Psychology, 23 (5), p. 543-558. (Year: 2011).*
SR Research, EyeLink II, 2001 (Year: 2001).*
SR Research, About Us—More than a Quarter Century History, 2001 (Year: 2001).*
"International Application Serial No. PCT US2015 033294, International Search Report dated Sep. 8, 2015", 2 pgs.
"International Application Serial No. PCT US2015 033294, Written Opinion dated Sep. 8, 2015", 6 pgs.
"International Application Serial No. PCT US2015 033294, International Preliminary Report on Patentability dated May 20, 2016", 8 pgs.
"International Application Serial No. PCT US2015 033294, International Preliminary Report on Patentability dated Aug. 4, 2016", 15 pgs.
Oride et al., "Reliability Study of the Pierce and King-Devick Saccade Tests", American Journal of Optometry & Physiological Optics, 1986, 63(6), 419-424.
Garzia et al., "A new visual-verbal saccade test: the development eye movement test (DEM)", J. Am. Optum. Assoc., 1990, 61,124-135.
Pang et al., "The Developmental Eye Movement (DEM) test and Cantonese-speaking children in Hong Kong SAR, China", Clinical and Experimental Optometry, Jul. 4, 2010, 93, 4, 213-223.

* cited by examiner

Prior Art
FIG. 2

TEST A 3 4
7 5
5 2
9 1
8 7
2 5
5 3
7 7
4 4
6 8
1 7
4 4
7 6
6 5
3 2
7 9
9 2
3 3
9 6
2 4

PRIOR ART
FIG. 3A

TEST B 6 7
3 9
2 3
9 9
1 2
7 1
4 4
6 7
5 6
2 3
5 2
3 5
7 7
4 4
8 6
4 3
5 7
2 5
1 9
7 8

PRIOR ART
FIG. 3B

TEST C 3   7 5     9   8
2 5   7   4   6
1   4 7   6   3
7   9 3   9   2
4 5   2   1   7
5   3 7   4   8
7 4 6 5     2
9   2   3   6 4
6 3 2 9     1
7     4 6 5   2
5   3 7   4   8
4   5 2   1   7
7 9 3   9     2
1   4   7 6   3
2   5 7   4   6
3 7 5     9   8

PRIOR ART
FIG. 3C

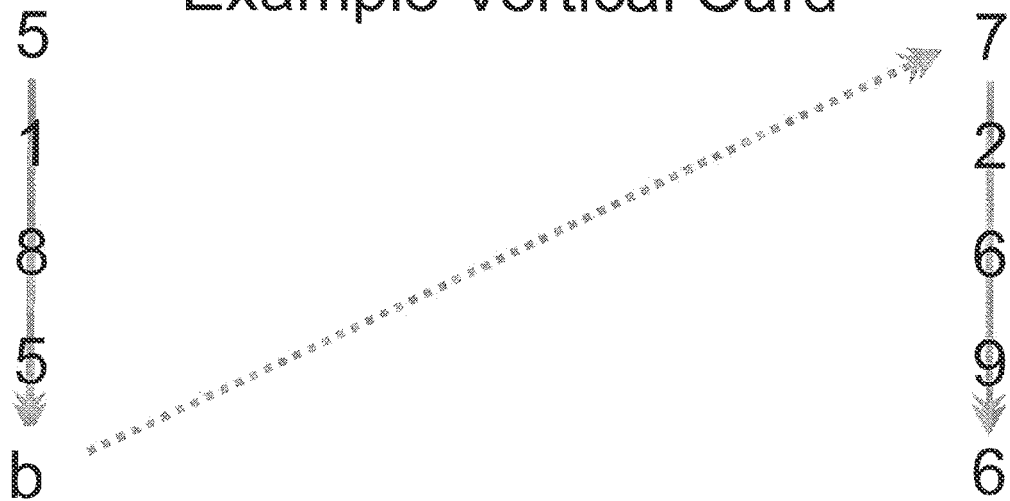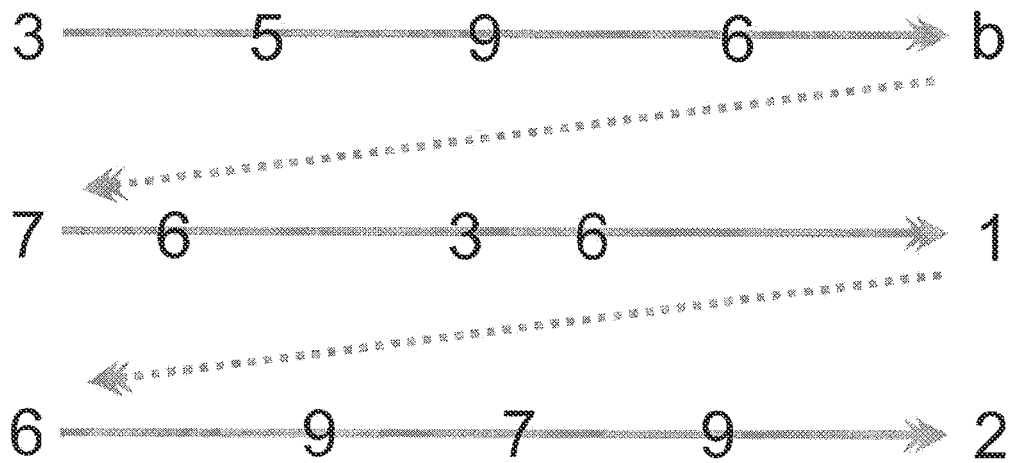
Fig. 4

|   |   |   |   |   |   |
|---|---|---|---|---|---|
| 8 |   | 6 | 9 | 7 | 6 |
| 8 | 5 | 9 |   | 1 | 8 |
| 6 |   | 9 | 5 | 6 | 8 |
| 3 |   | 5 | 9 | 6 | 8 |
| 7 | 6 |   | 3 | 6 | 1 |
| 6 |   | 9 | 7 | 9 | 2 |
| 7 | 6 | 9 |   | 6 | 1 |
| 2 |   | 8 | 5 | 8 | 2 |

Card A 8697685918695683598 6 8

7 6 3 6 1 6 9 7 9 2 7 6 9 6 1 2 8 5 8 2

Card B 8 6 9 7 6 D C B E B 6 9 5 6 8 D B A D C 7 6 3 6 1 9 2 B 9 D 7 6 9 6 1 9 C E 1 2

Card C

| 8 |   | 6 |   | 9 |   | 7 |   | 6 |
| 8 | 5 |   | 9 |   |   |   | 1 | 8 |
| 6 |   |   | 9 | 5 |   | 6 |   | 8 |
| 3 |   | 5 |   | 9 |   | 6 |   | 8 |
| 7 | 6 |   |   | 3 | 6 |   |   | 1 |
| 6 |   |   | 9 |   | 7 | 9 |   | 2 |
| 7 | 6 |   | 9 |   |   | 6 |   | 1 |
| 2 |   | 8 |   |   | 5 | 8 |   | 2 |

Card D

| 8 |   | 6 |   | 9 |   | 7 |   | 6 |
| D | C |   | B |   |   |   | E | B |
| 6 |   |   | 9 | 5 |   | 6 |   | 8 |
| D |   | B |   | A |   | D |   | C |
| 7 | 6 |   |   | 3 | 6 |   |   | 1 |
| 9 |   |   | 2 |   | B | 9 |   | D |
| 7 | 6 |   | 9 |   |   | 6 |   | 1 |
| 9 |   | C |   |   | E | 1 |   | 2 |

| FIG. 10A | | FIG. 10B | |
|---|---|---|---|
| 4 | 1 | 4 | 1 |
| 5 | 6 | 5 | 6 |
| 9 | 2 | 9 | 2 |
| 2 | 9 | 2 | 9 |
| 6 | 8 | 6 | 8 |
| 2 | 3 | D | 3 |
| 7 | 7 | C | 7 |
| 2 | 1 | B | B |
| 4 | 5 | E | 5 |
| 2 | 2 | B | D |
| 5 | 1 | 5 | 1 |
| 2 | 3 | 2 | 3 |
| 6 | 7 | 6 | 7 |
| 7 | 2 | 7 | 2 |
| 3 | 4 | 3 | 4 |
| 8 | 7 | D | 7 |
| 1 | 5 | B | C |
| 3 | 6 | A | E |
| 4 | 3 | D | 3 |
| 6 | 1 | C | 1 |

| FIG. 10C | | FIG. 10D | |
|---|---|---|---|
| 4 | 1 | 4 | 1 |
| 7 | 6 | 7 | 6 |
| 1 | 2 | 1 | 2 |
| 2 | 9 | B | 9 |
| 6 | 8 | 6 | 8 |
| D | 3 | D | 3 |
| C | 7 | C | 7 |
| B | B | D | B |
| E | 5 | E | 5 |
| B | D | D | D |
| 7 | 1 | 7 | 1 |
| 2 | 3 | B | 3 |
| 6 | 7 | 6 | 7 |
| 9 | 2 | 9 | 2 |
| 5 | 4 | 5 | 4 |
| D | 7 | D | 7 |
| B | C | D | C |
| A | E | 2 | E |
| D | 3 | D | 3 |
| C | 1 | C | 1 |

| 4 | 5 | | 9 | | | 2 | | 6 |
|---|---|---|---|---|---|---|---|---|
| 2 | | 7 | 2 | | 4 | | | 2 |
| 5 | | 2 | | 6 | | 7 | | 3 |
| 8 | 1 | | | 3 | 4 | | | 6 |
| 1 | | | 6 | | 2 | | 9 | 8 |
| 3 | 7 | | 1 | | 5 | | | 2 |
| 1 | | 3 | | | 7 | 2 | | 4 |
| 7 | 5 | | 6 | | | 3 | | 1 |

Fig. 13B

| 4 | 5 | | 9 | | | 2 | | 6 |
|---|---|---|---|---|---|---|---|---|
| D | | C | B | | E | | | B |
| 5 | | 2 | | 6 | | 7 | | 3 |
| D | B | | | A | D | | | C |
| 1 | | | 6 | | 2 | | 9 | 8 |
| 3 | 7 | | B | | 5 | | | D |
| 1 | | 3 | | | 7 | 2 | | 4 |
| 7 | C | | E | | | 3 | | 1 |

Fig. 13C

| 4 | 5 | | 9 | | | 2 | | 6 |
|---|---|---|---|---|---|---|---|---|
| D | | C | B | | E | | | B |
| 5 | | 2 | | 6 | | 7 | | 3 |
| D | B | | | A | D | | | C |
| 1 | | | 6 | | 2 | | 9 | 8 |
| 3 | 7 | | B | | 5 | | | D |
| 1 | | 3 | | | 7 | 2 | | 4 |
| 7 | C | | E | | | 3 | | 1 |

MULTIMODAL HEALTH ASSESSMENT WITH NEURO-OPTHALMOLOGICAL SACCADE TESTS

CROSS REFERENCE TO RELATED APPLICATIONS

This application is a National Stage Application filed under 35 U.S.C. § 371 of International Application No. PCT/US2015/033294, filed May 29, 2015, which claims benefit of Provisional Application No. 62/005,639, filed May 30, 2014. The contents of both patent applications are hereby incorporated by reference in their entireties.

TECHNICAL FIELD

The invention relates to diagnosis and analysis of brain health through the use of neuro-ophthalmological saccade and eye movement tests in a system to dynamically assess one's brain state and function.

BACKGROUND

Normal functioning of the brain and central nervous system is critical to a healthy, enjoyable and productive life. Disorders of the brain and central nervous system are among the most dreaded of diseases. Many neurological disorders such as stroke, Alzheimer's disease, and Parkinson's disease are insidious and progressive, becoming more common with increasing age. Others such as schizophrenia, depression, multiple sclerosis and epilepsy arise at younger age and can persist and progress throughout an individual's lifetime. Sudden catastrophic damage to the nervous system, such as brain trauma, infections, cancer, and intoxications can also affect any individual of any age at any time.

Most nervous system dysfunction arises from complex interactions between an individual's genotype, environment and personal habits and thus often presents in highly personalized ways. However, despite the emerging importance of preventative health care, convenient means for objectively assessing the health of one's own nervous system have not been widely available. Therefore, new ways to monitor the health status of the brain and nervous system are needed for normal health surveillance, early diagnosis of dysfunction, tracking of disease progression and the discovery and optimization of treatments and new therapies.

Neuro-ophthalmologic saccade tests (or saccade tests) have been used for decades. One of the first reported was the Pierce Saccade test which consisted of 15 rows of two numbers per row (Oride M. K H., et al, 1986. Reliability Study of the Pierce and King-Devick Saccade Tests. *Amer J. Optom & Physiol Optics*, v63(6):419-424). The first card was a demonstration card with arrows indicating the path of the eye both across each row and down the card. The first test card A lacked the vertical arrows but maintained the horizontal saccade arrows to aid the eye. The $2^{nd}$ card B lacked the horizontal arrows while the third card C compressed the vertical dimension between rows of numbers making eye tracking a more difficult task. The vertical spacing of the A and B cards was ½ inch while the vertical spacing of the third card C was 5/16 inch. Scoring was based on the total time to read cards A, B, and C summed together as well as the number of errors and omissions recorded by the test administrator. Performance is then evaluated by comparing the total corrected time (time corrected for errors) to age norms supplied with the test.

In 1986, King and Devick published an improvement increasing the number of elements on a given row from two (2) to five (5) elements, thereby differentiating horizontal saccades between fixations from the vertical saccades back to the beginning of a new row of elements, in this case single digit numbers (Oride M. K H., et al, 1986. Reliability Study of the Pierce and King-Devick Saccade Tests. *Amer J. Optom & Physiol Optics*, v63(6):419-424 and refs therein). The test consists of one demonstration card and three test cards which get progressively harder. The first test card lacks the vertical arrows to assist the subject. The second test card is lacking the horizontal arrows to assist the subject. Finally, the last card is squeezed in the vertical dimension creating increased probability of error unless one works hard to stay focused on the task at hand. The three test cards are read twice in succession with the total time for the set of three cards (as measured by a stop watch) with the minimum number of errors as the final task output performance variable, based on the minimum number of errors as determined by the test administrator listening along.

In 1990, the Developmental Eye Movement (DEM) test was published to improve on the King-Devick test by de-convolving the ability to name numbers aloud (automaticity in number calling skills) from saccadic performance and ocular motility (Garzia R P, Richman J E, Nicholson S B, Gaines C S. A new visual-verbal saccade test: the development eye movement test (DEM). *J Am Optom Assoc* 1990; 61:124-35). The test consists of one pre-test card, 2 vertical test cards A and B which consist of two columns of 20 single digit numbers each, followed by a single final horizontal test card C, which consists of the same 80 numbers from cards A and B but arranged horizontally in 16 rows of 5 single digit numbers each. The vertical time VT is the sum of time in seconds necessary to complete both cards A and B (not accounting for any errors). The VT reflects the time it takes to read aloud 80 numbers arranged vertically (20 per column in a total of 4 columns across cards A and B). The Adjusted Horizontal Time AHT is the time of card C adjusted for omission or addition Errors, where AHT=(Raw Card C Time*80)/(80−additions+omissions). The AHT reflects the total time to read aloud the same 80 numbers arranged in a horizontal pattern and the time to perform saccadic eye movements from number to number. A Ratio score of horizontal to vertical is calculated by dividing the AHT by the VT, where Ratio=AHT/VT. The total error reflects the total number of Errors in the final horizontal C card (i.e. sum of omissions, additions, substitutions, and transpositions).

The interpretation of the test is defined by the Ratio score as a measure of ocular motility dysfunction. It can also be used to determine a problem with automaticity in number reading that may indirectly reflect a dysfunction in sustained attention, visuo-spatial attention, number recognition, speaking time, phonological process or other cognitive problem. To determine the percentile or standard score for the VT, AHT, Ratio and Error, it is necessary to consult normative data tables as published in the literature.

Unlike cardiovascular and metabolic disorders, where personalized health monitoring biomarkers such as blood pressure, cholesterol, and blood glucose have long become household terms, no such convenient biomarkers of brain and nervous system health exist. Quantitative neurophysiological assessment approaches such as positron emission tomography (PET), functional magnetic resonance imaging (fMRI) and neuropsychiatric or cognition testing involve significant operator expertise, inpatient or clinic-based testing and significant time and expense. Moreover, such assessments most often include the subjective opinion of a human clinician. One potential technique that may be adapted to serve a broader role as a facile biomarker of nervous system function is a multimodal assessment of the brain from a number of different forms of data, including electroencephalography (EEG), which measures the brain's ability to generate and transmit electrical signals. However, formal lab-based EEG approaches typically require significant operator training, cumbersome equipment, and are used primarily to test for epilepsy. Again, most often EEG assessments include the opinion of a clinician. Additional modalities can include voice recognition for verbal tasks that require a response from the individual or eye tracking which non-invasively measures the individual location of the eye gaze (x, y) as a function of time (t) while the subject participates in voluntary or non-voluntary tasks.

Alternate and innovative biomarker approaches are needed to provide quantitative measurements of personal brain health that could greatly improve the prevention, diagnosis and treatment of neurological and psychiatric disorders. Objective biomarkers are desired that can be used to help in the selection of drugs or therapy for a patient. Objective biomarkers also can be used to identify drugs and therapies that are working, to enroll patients in investigative clinical trials, or to select patients appropriate for a given therapy, a so-called "companion diagnostic." In addition, objective biomarkers can be used to monitor and measure disease progression or the prognosis of a subject for a given potential condition in the future as well as for a baseline assessment of a subject in order to have a within subject comparison at a later time, especially if something bad or untoward has occurred or if one is trying to prevent something bad from happening. Such a case would be well exemplified using objective biomarkers to help in the identification of subjects at risk for suicide, a major problem with warfighters after the conflict is over and they have returned to civilian life. Identifying unique multimodal devices and tests that lead to biomarkers of Parkinson's disease, Alzheimer's disease, concussion and other neurological and neuropsychiatric conditions like depression and schizophrenia is a pressing need.

Alternate and innovative biomarker approaches are also able to provide quantitative measurements of personal brain health that could be useful in non-traditional medical use cases such as insurance claims processing, marital relationship work, and employee team building in the workplace. In the case of worker's compensation claims processing, objective biomarkers could be used to support or refute the medical basis for a given claim, such as concussion or head injury, neck or soft-tissue pain or other "invisible" injury. Moreover, objective biomarkers could be useful in the claims processing for disability insurance as well as risk management for liability in athletics programs of interest. In the case of couples therapy, objective biomarkers could be useful to provide both clinicians and participants with objective data on which to modify behaviors and improve relationships. This could equally be useful in the work place where team dynamics could be enhanced with objective biomarkers to enable various departments and functions within a team to better get along. Lastly, objective biomarkers could be useful in the employment hiring business and promotion process to identify proper candidates with the proper temperament for a given position or role. The military could use objective biomarkers to select soldiers with resilience or commanders with the proper response to challenge and uncertainty. Today, these are all soft decisions made off subjective evaluations. A more objective approach is desired.

SUMMARY OF THE INVENTION

A system and methods addressing the above-mentioned needs in the art includes a plurality of biological sensors adapted to collect biological sensor data from the subject as well as the ability to stimulate the brain in a variety of sensory, cognitive, physical, and chemical challenges. Saccade cards are employed to measure the health of a subject through collection of eye tracking data. Saccade cards using a variety of design elements besides numbers are used for collection of the eye tracking data. The saccade data is used as part of the brain health assessment and may be used as an objective biomarker for such brain health assessments.

In exemplary embodiments, the invention includes a system for capturing biological sensor data for assessing brain health of a subject. The brain health assessment system includes a plurality of biological stimulation devices that simultaneously record biological sensor data from the subject in response to biological stimulation. In exemplary embodiments, the biological stimulation devices include an eye saccade test that is presented to the subject to measure saccadic performance and ocular motility. A recording device records as an objective biomarker of the brain health of the subject the biological sensor data collected from the subject including responses of the subject at different points in time in response to the presentation of the eye saccade test to the subject.

In particular embodiments, the eye saccade test includes presentation of at least one eye saccade card that has at least one set of non-numerical elements. In an exemplary embodiment, the at least one eye saccade card includes a first set of elements selected from single digit numbers from zero to nine {0, 1, 2, 3, 4, 5, 6, 7, 8, 9} and a second set of elements selected from at least one of the following: the first six capital letters of the alphabet {A, B, C, D, E, F}, 2 digit numbers, 3 or more digit numbers, upper case letters of the alphabet {A, B, C, D, E, F, G, H, I, J, K, L, M, N, O, P, Q, R, S, T, U, V, W, X, Y, Z}, lower case letters of the alphabet {a, b, c, d, e, f, g, h, i, j, k, l, m, n, o, p, q, r, s, t, u, v, w, x, y, z}, two letter words with either uniform case or mixed case, three letter words with either mixed case or uniform case, foreign language characters, letter schemes, text of various colors and sizes, shift in font from normal to italics or bold-face or underlined, graphical ASCII characters above the digits from the group comprising: !, @, #, $, %, ^, &, *, and (, ), and icons indicating direction or emotion. The at least one eye saccade card may also include a first saccade eye card including a column of vertical elements from the first and/or second set of elements in a first order from top to bottom on the first saccade eye card and a second saccade eye card including a row of horizontal elements corresponding to the elements in the column of vertical elements on the first saccade card except that the horizontal elements are disposed in the first order from left to right on the second saccade eye card.

In exemplary embodiments of the system, the biological sensors include an eye tracking device that monitors the response of the subject in response to the presentation of at least one eye saccade card to visually stimulate the subject. The eye tracking device may include means for monitoring the eye position and response of the subject in response to the presentation of the at least one eye saccade card to the subject. The eye position monitoring means may include an electrical potential measuring device that measures an electrical potential generated across an orbit eye cavity or a web camera that determines retinal position, for example.

The invention further includes a method for assessing brain health of a subject, comprising the steps of presenting an eye saccade test to the subject, recording biological sensor data from the subject in response to presentation of the eye saccade test, and measuring saccadic performance and ocular motility from the biological sensor data. In exemplary embodiments, the eye saccade test includes presenting at least one saccade card that has at least one set of non-numerical elements. The method may further include repeating the presenting, recording, and measuring steps to identify changes in the saccadic performance and ocular motility of the subject over time. The method also may include correlating the identified changes in the saccadic performance and ocular motility of the subject over time to a brain health condition of the subject. For example, the identified changes in the saccadic performance and ocular motility of the subject over time may be used to construct a multi-variate signature of the brain health condition of the subject.

These and other features of the invention will be apparent from the following detailed description.

BRIEF DESCRIPTION OF THE DRAWINGS

Embodiments of the invention can be better understood with reference to the following drawings, of which:

FIG. 2 is a schematic diagram illustrating prior art versions of saccade card tasks, in this case the King-Devick saccade test.

FIG. 3 is a schematic diagram illustrating prior art versions of saccade card tasks, in this case the Developmental Eye Movement (DEM) task.

FIG. 4 is an example of practice cards of the novel saccade task of the present invention which includes not only numbers but also letters, creating a mixed set of characters or elements to recognize.

FIG. 5C is an example of easy horizontal saccade card of the novel saccade task of the present invention which may or may not include letters or other disjoint elements (not only numbers), creating a mixed set of characters or elements to recognize.

FIG. 5D is an example of more difficult horizontal saccade card of the novel saccade task of the present invention which includes letters or other disjoint elements (not only numbers), creating a mixed set of characters or elements to recognize.

FIG. 6 is a schematic illustration of an ensemble of saccade cards within the scope of the present invention.

FIG. 7 is a schematic illustration of a horizontal saccade card with decreased row spacing and hence increased spatial frequency.

FIG. 8 is a schematic illustration of a horizontal saccade card with decreased row spacing and hence increased spatial frequency, but also a third set of elements, in this case lower case letters such as "b" and "e".

FIG. 9 is a schematic illustration of a horizontal saccade card with decreased row spacing and hence increased spatial frequency, but also a fourth set of elements, in this case lower case letters such as "e" as well as characters such as "$", "&" and "@". It also illustrates the possibility to include color shift between sets.

FIG. 10A is a schematic illustration of a Vertical Card A.

FIG. 10B is a schematic illustration of a Vertical Card B which now includes the secondary set of elements.

FIG. 10C is a schematic illustration of a Vertical Card B (FIG. 10B) which now includes the orderly permuted elements of 1 to 3, 3 to 5, 5 to 7, 7 to 9, and 9 to 1 in the left column of elements (right column remains unchanged for illustration purposes).

FIG. 10D is a schematic illustration of a Vertical Card B (FIG. 10B) which now includes the orderly permuted elements of 1 to 3, 3 to 5, 5 to 7, 7 to 9, and 9 to 1 as in FIG. 10C but also the stochastically permuted elements of A to 2, 2 to B, B to D in the left column of elements (right column remains unchanged for illustration purposes).

FIGS. 11A-11C are schematic illustrations of a variant Vertical Card B.

FIGS. 13A-13C are schematic illustrations of a horizontal Card C.

DETAILED DESCRIPTION OF ILLUSTRATIVE EMBODIMENTS

Figure 1:
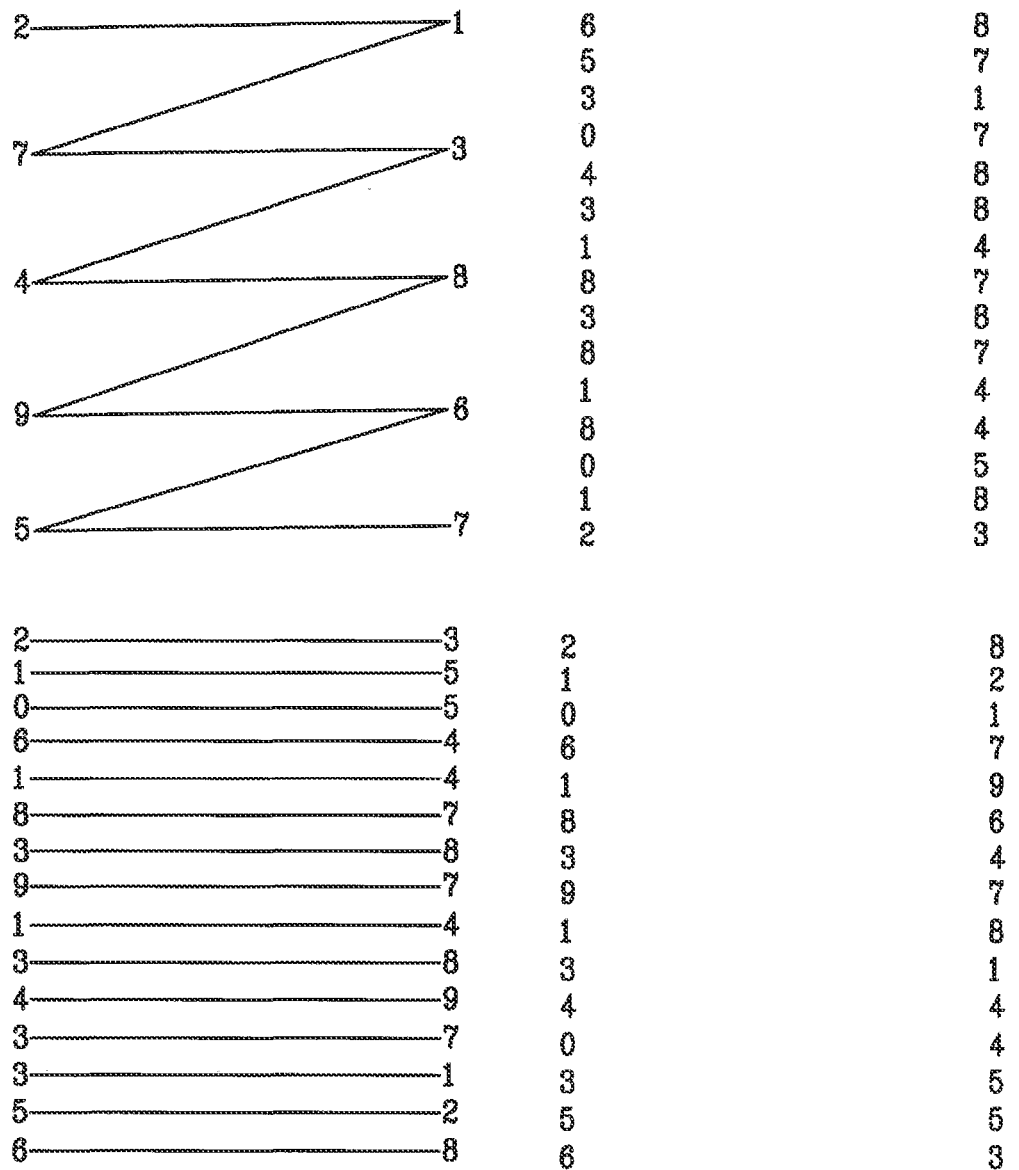
FIG. 1 is a schematic diagram illustrating prior art versions of saccade card tasks, starting with the Pierce saccade task.

The invention will be described in detail below with reference to FIGS. 1-16. Those skilled in the art will appreciate that the description given herein with respect to those figures is for exemplary purposes only and is not intended in any way to limit the scope of the invention. All questions regarding the scope of the invention may be resolved by referring to the appended claims.

Definitions

By "monitor the brain and nervous system" we mean to include, without limitation, surveillance of normal health and aging, the early detection and monitoring of brain dysfunction, monitoring of brain injury and recovery, monitoring disease onset, progression and response to therapy, for the discovery and optimization of treatment and drug therapies, including without limitation, monitoring investigational compounds and registered pharmaceutical agents, as well as the monitoring of illegal substances and their presence or influence on an individual while driving, playing sports, or engaged in other regulated behaviors.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

By "EEG data" we mean to include without limitation the raw time series, any spectral properties determined after Fourier transformation, any nonlinear properties after nonlinear analysis, any wavelet properties, any summary biometric variables and any combinations thereof.

A "sensory and cognitive challenge" as used herein is intended to encompass any form of sensory stimuli (to the five senses), cognitive challenges (to the mind), and other physiological challenges (such as a respiratory $CO_2$ challenge, virtual reality balance challenge, hammer to knee reflex challenge, etc.).

A "sensory and cognitive challenge state" as used herein is intended to encompass any state of the brain and nervous system during the exposure to the sensory and cognitive challenge.

An "electronic system" as used herein is intended to encompass, without limitation, hardware, software, firmware, analog circuits, DC-coupled or AC-coupled circuits, digital circuits, FPGA, ASICS, optical circuits, audio circuits, visual displays, audio transducers, temperature generators or transducers, olfactory and odor generators, or any combination of the above.

By "spectral bands" we mean without limitation the generally accepted definitions in the standard literature conventions such that the bands of the PSD are often separated into the Delta band (f<4 Hz), the Theta band (4<f<7 Hz), the Alpha band (8<f<14 Hz), the Beta band (14<f<30 Hz), and the Gamma band (30<f<100 Hz). The exact boundaries of these bands are subject to some interpretation and are not considered hard and absolute to all practitioners in the field.

By "calibrating" we mean the process of putting known inputs into the system and adjusting internal gain, offset or other adjustable parameters in order to bring the system to a quantitative state of reproducibility.

By "conducting quality control" we mean conducting assessments of the system with known input signals and verifying that the output of the system is as expected. Moreover, verifying the output to known input reference signals constitutes a form of quality control which assures that the system was in good working order either before or just after a block of data was collected on a human subject.

By "biomarker" we mean an objective measure of a biological or physiological function or process.

By "biomarker features or metrics" we mean a variable, biomarker, metric or feature which characterizes some aspect of the raw underlying time series data. These terms are equivalent for a biomarker as an objective measure and can be used interchangeably.

By "non-invasively" we mean lacking the need to penetrate the skin or tissue of a subject.

By "diagnosis" we mean any one of the multiple intended use of a diagnostic including to classify subjects in categorical groups, to aid in the diagnosis when used with other additional information, to screen at a high level where no a priori reason exists, to be used as a prognostic marker, to be used as a disease or injury progression marker, to be used as a treatment response marker or even as a treatment monitoring endpoint.

By "electronics module" or "EM" or "reusable electronic module" or "REM" or "multi-functional biosensor" or "MFB" we mean an electronics module or device that can be used to record biological signals from the same subject or multiple subjects at different times. By the same terms, we also mean a disposable electronics module that can be used once and thrown away which may be part of the future as miniaturization becomes more common place and costs of production are reduced. The electronics module can have only one sensing function or a multitude (more than one), where the latter (more than one) is more common. All of these terms are equivalent and do not limit the scope of the invention.

By "biosignals" or "bio signals" or "bio-signals" we mean any direct or indirect biological signal measurement data streams which either directly derives from the human subject under assessment or indirectly derives from the human subject. Non-limiting examples for illustration purposes include EEG brainwave data recorded either directly from the scalp or contactless from the scalp, core temperature, physical motion or balance derived from body worn accelerometers, gyrometers, and magnetic compasses, the acoustic sound from a microphone to capture the voice of the individual, the stream of camera images from a front facing camera, the heart rate, heart rate variability and arterial oxygen from a would pulse oximeter, the skin conductance measured along the skin, the cognitive task information recorded as keyboard strokes, mouse clicks or touch screen events. There are many other biosignals to be recorded as well.

By "neuro-opthalmological saccade task" or "saccade task" or "eye movement task" we mean any direct or indirect task designed to challenge the ability of the eyes to properly perform in the normal course of daily life. This could include investigations of fixations, saccades or other more detailed features of the trajectory of a subject's eyes in time during a health evaluation. The saccade task could include an eye saccade test that includes presentation of one or more saccade cards of the type described herein. The saccade cards could be presented manually or visually on a computer screen. Thus, a "saccade card" as used herein could mean a paper card, an electronic card, or an optical means for stimulating the visual field with light to present the saccadic data.

By "subject" we mean the person receiving the saccade test. The "subject" may also be referred to as a "user" or "patient."

Progression from Pierce to King-Devick to DEM Cards

The systems and methods of the prevention invention build on the literature in a novel fashion. Rather than rely solely on numbers for the DEM, the system and methods of the present invention comprise saccade cards that include at least two distinct sets of elements, whether that is numbers and letters, numbers and symbols, or letters and symbols. Other examples of mixed elements could include upper and lower case letters, color of the foreground letter or background, size, font type, or texture. Symbols could equally be used such that elements could indicate direction, simple or complex geometric shapes, familiar and novel symbols, or characters from a non-native language.

Figure 2:
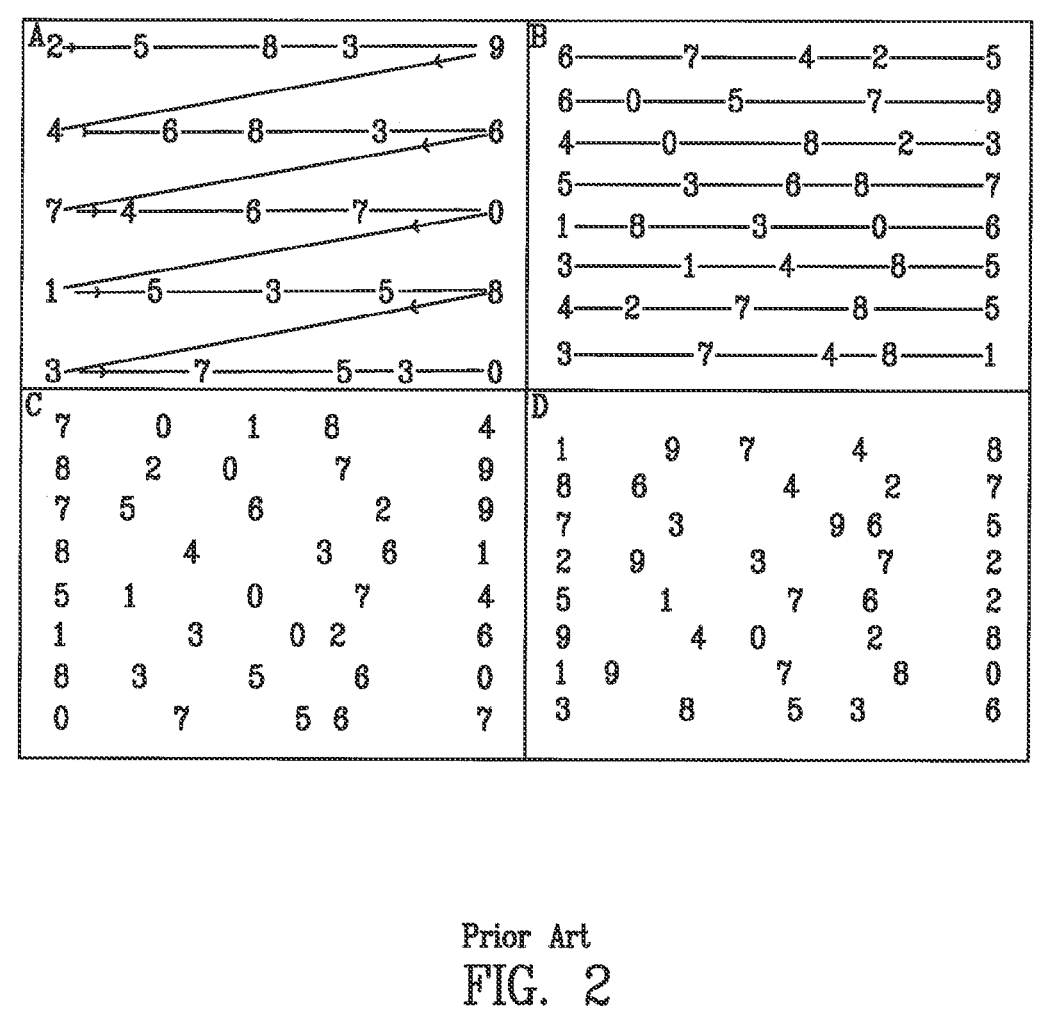

Examples of prior art saccade tasks can be found in FIGS. 1, 2, and 3. FIG. 1 illustrates the saccade cards of the Pierce saccade task which consists of two columns of numbers. The subject is asked to read the numbers left to right, top to bottom, as fast as they can without errors. The first card is a practice card (upper left) which has arrows installed to guide the eye of the subject to instruct them. On a first test card, the vertical saccade arrows are missing (lower left) and on the second test card (upper right) there are no arrows to guide the eye. Lastly on the third test card (lower right), there are no arrows but now with decreased vertical line spacing, thus increased spatial frequency, designed to make the challenge progressively harder on each test card.

FIG. 2 shows the demonstration card and three Saccade cards from the King-Devick test which represents an improvement on the Pierce saccade task by utilizing multiple horizontal saccades before asking for a vertical saccade back to the first element of the next lowest row. The task consists of 8 rows of 5 elements each for a total of 40 elements on each card. After a demonstration card with a full set of arrows to guide the eye and train the subject (FIG. 2A), the cards get successively more difficult by removing the vertical arrows on the first card (FIG. 2B), removing the horizontal arrows on the second card (FIG. 2C), and decreasing the interline spacing with increased spatial frequency on the third card (FIG. 2D). This set of three progressively more difficult cards is repeated a second time. The lowest sum of time for three cards with the minimum number of errors is the overall outcome performance score (as measured in seconds) for the K-D test.

Lastly, in FIG. 3, one can see the DEM saccade cards which now consist of two vertical cards (Test A and Test B) with 20 numbers in the first column and 20 numbers in the second column of each card (See FIG. 3A and FIG. 3B). The third card is a horizontal card similar to the K-D test cards arranged with 16 rows of 5 elements per row. However, in the DEM saccade cards, now the speed at which numbers are read in the vertical dimension can be de-convolved from the horizontal cards to adjust for individual differences in auditory number reading capability.

Novel Saccade Cards that Involve Two or More Sets of Differentiated Elements

An aspect of the present invention includes using at least two distinguished sets of elements for the saccade task cards rather than a single set of elements. For instance, in one embodiment as illustrated in FIG. 4, a demonstration card can include both vertical and horizontal examples of the task. In a preferred embodiment, the demonstration card includes at least two distinct sets of elements so that the subject must shift from one set of elements (the more common or frequent one) to a distinct or disjoint set of elements. In the present embodiment, the single digit numbers from zero to nine {0, 1, 2, 3, 4, 5, 6, 7, 8, 9} include the primary set of elements from which a second set of elements, for example, the first six capital letters of the alphabet {A, B, C, D, E, F}, form the secondary or infrequent set from which set-shifted elements are selected. This embodiment is essentially a shift from a decimal system of ten elements to a hexadecimal system of sixteen elements.

Figure 5A:
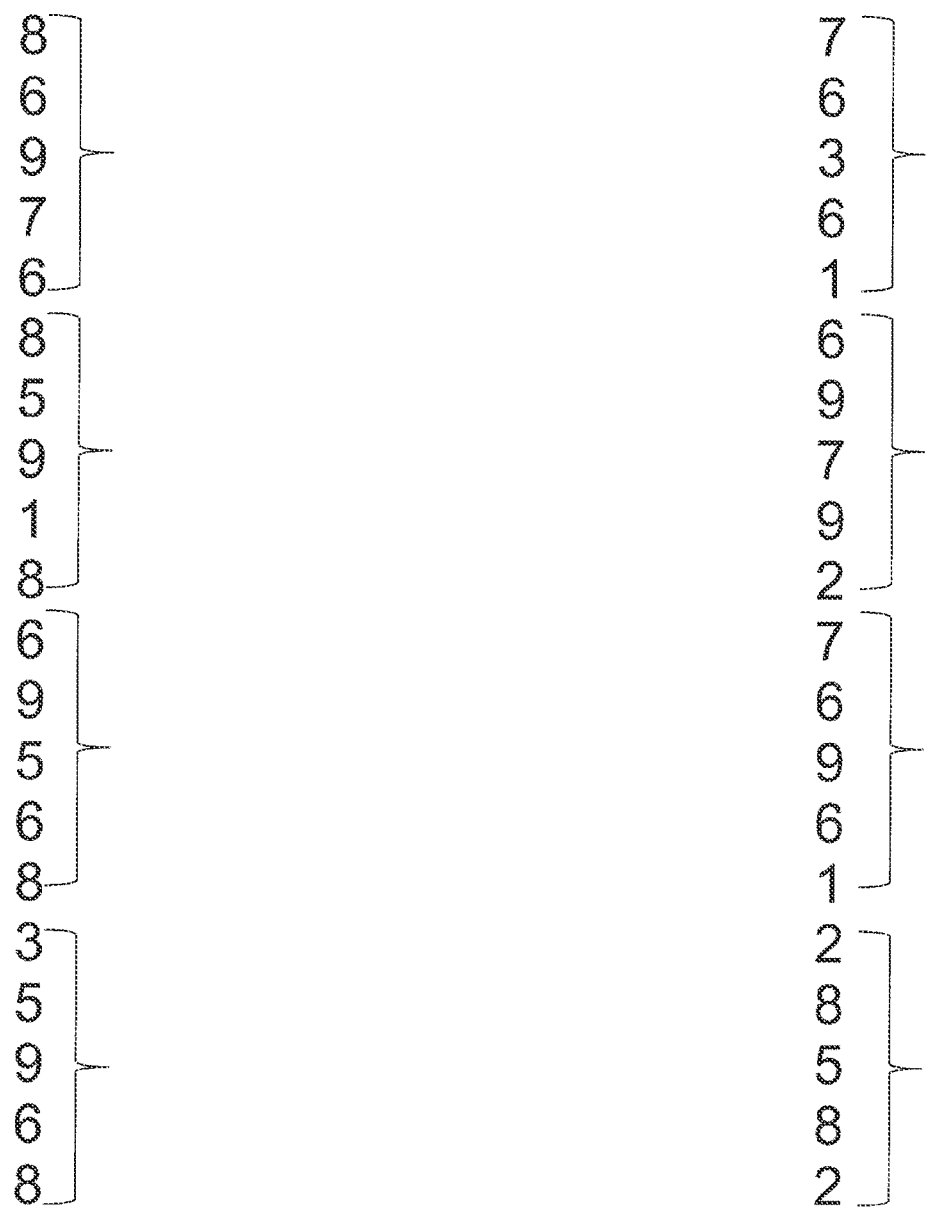
FIG. 5A is an example of easy vertical saccade card of the novel saccade task of the present invention which may or may not include letters or other disjoint elements (not only numbers), creating a mixed set of characters or elements to recognize.
Figure 5B:
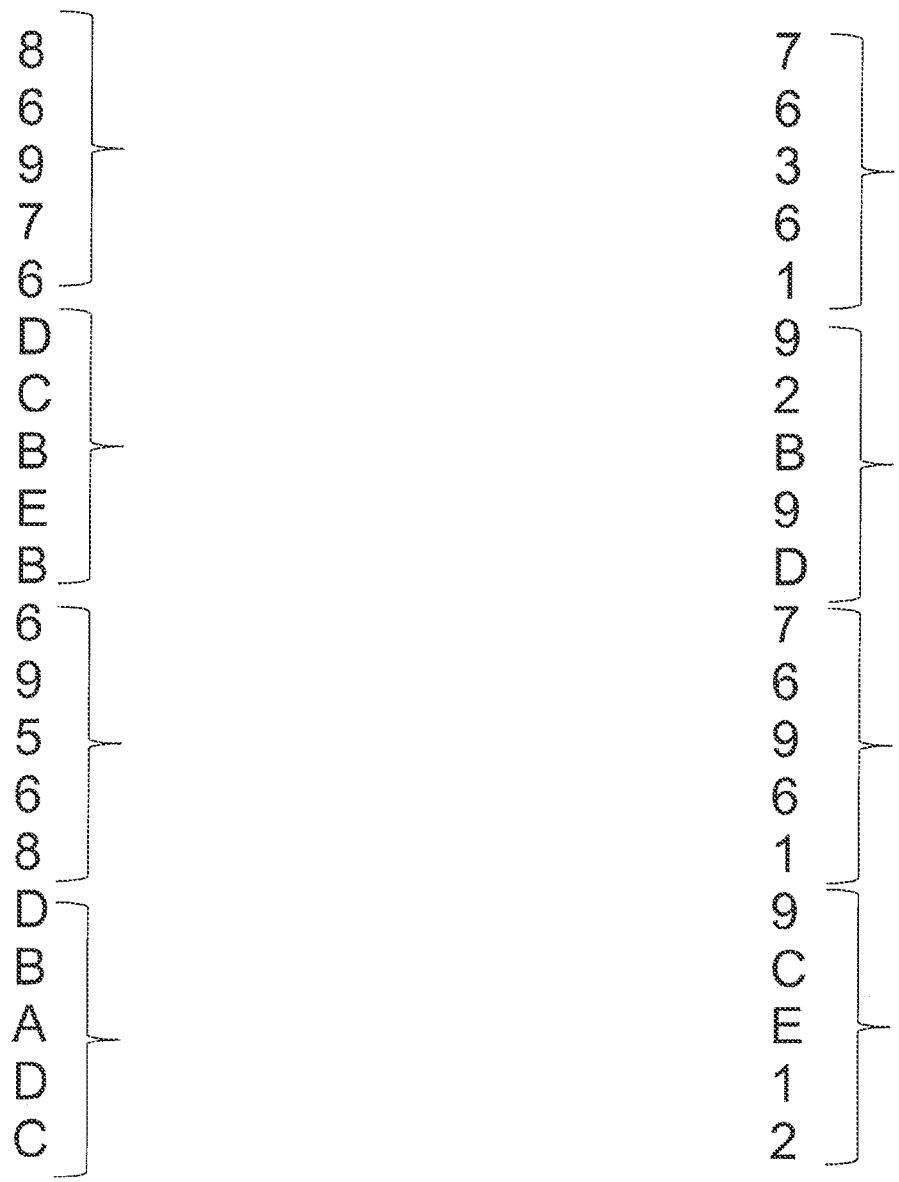
FIG. 5B is an example of more difficult vertical saccade card of the novel saccade task of the present invention which includes letters or other disjoint elements (not only numbers), creating a mixed set of characters or elements to recognize.

The first two test cards assess a subject's ability to automatically name numbers without saccade in a vertical stack on a sheet of paper or computer visual display. In one embodiment as illustrated in FIG. 5A, a first vertical naming card has 20 elements in a left hand column followed by 20 elements in a second column to the right. As can be seen by the brackets in the FIG. 5A, each group of 5 elements on the vertical card will become a row on the horizontal card to follow, in a similar fashion to the DEM. Thus, the eventual comparison between horizontal read time and vertical read time are for the same exact list of elements within a given task. The elements on the first card shown in FIG. 5A are all from the primary set of elements, in this case the ten elements including single digit numbers. The second vertical naming card, shown as FIG. 5B, is similar to the first, but now has elements from the second non-primary set included on the card. In this illustrative embodiment, the second set of elements includes the first six capitalized letters of the alphabet, also known as the hexadecimal system. In FIG. 5B, one can see by the brackets to the right, sequences of 5 elements that are all the primary set (single digit numbers such as 86976), all the secondary set (capital A through F such as DCBEB), and some sequences that are a mixture of the primary set with the secondary set (e.g. 9CE12).

The second two test cards assess a subject's ability to automatically name numbers with saccade in a horizontal row arrangement on a sheet of paper or computer visual display or other display device. In one embodiment, as illustrated in FIG. 5C, a first horizontal naming card has 8 rows of 5 elements each. As can be seen by the brackets in the FIG. 5A, each row of FIG. 5C aligns in exact order with a group of 5 elements from the first card shown in FIG. 5A, only now transposed horizontally instead of vertically. The second horizontal test card, shown as an embodiment in FIG. 5D, has again 8 rows of 5 elements each. In this case, the either all primary, all secondary or mixed primary and secondary sequences of elements which were listed on the second vertical card (FIG. 5B) are now listed as either all primary (top row), all secondary (second row) or mixed primary and secondary elements (i.e. the last row of the figure).

As shown in FIG. 6, the cards of FIG. 5A through FIG. 5D are arranged together to emphasize the structure of the novel saccade cards. The full set of saccade cards (two vertical followed by two horizontal) can see seen in FIG. 6. In another embodiment, shown as FIG. 7, the size of the font has increased among other shifts including the use of a row of secondary elements (in this case all capital letters in the second row from the top) as well as the relative spacing between elements. In FIG. 8, one can see an embodiment which includes lower case letters in addition to upper case letters. In FIG. 9, one can see the further incorporation of a fourth set of elements, in this case the control characters "$", "&", "@" highlighted in an alternate color, another shift which can be used to effectively change the quality and character of the particular embodiment of the present invention.

Figure 12A:
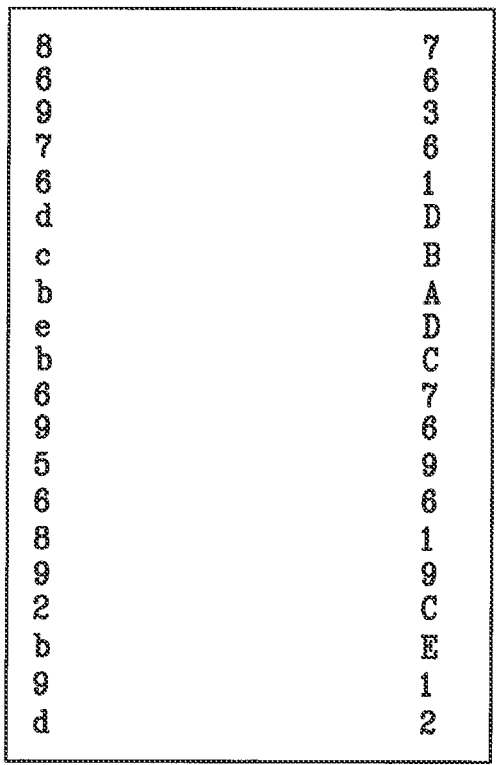
FIGS. 12A-12D are schematic illustrations of a variant Vertical Card B.
Figure 12B:
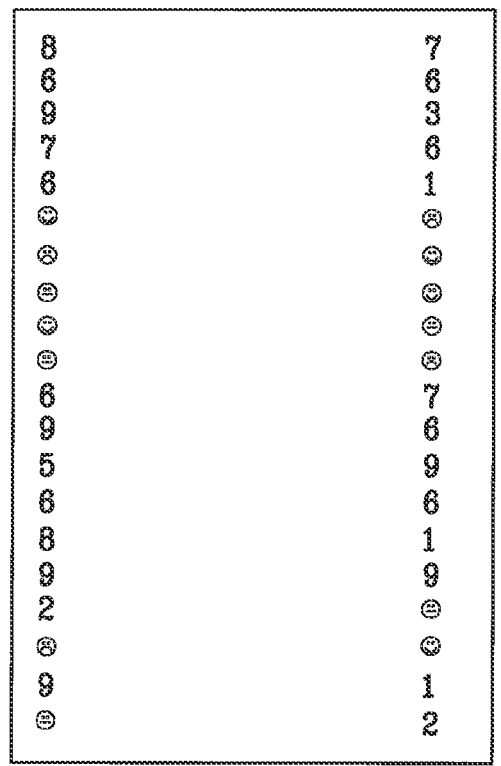

Other primary and secondary sets of elements can be contemplated. Non-limiting examples of what other element sets could be beyond single digit numbers {0, 1, 2, 3, 4, 5, 6, 7, 8, 9, 0} and the first six capital letters {A, B, C, D, E, F}, including 2 digit numbers, e.g. {10, 14, 18, 19, 33, 88, 91} and higher order numbers of various lengths e.g. {140, 138, 483, 388, 977}, upper case letters of the alphabet {A, B, C, D, E, F, G, H, I, J, K, L, M, N, O, P, Q, R, S, T, U, V, W, X, Y, Z}, lower case letters {a, b, c, d, e, f, g, h, i, j, k, l, m, n, o, p, q, r, s, t, u, v, w, x, y, z}, two letter words with either uniform case or mixed case {to, in, of, To, In, Of, TO, IN, OF}, three letter words with either mixed case or uniform case {cat, hat, and, the, few, tin, bin, Cat, Hat, And, The, Few, Tin, Bin, CAT, HAT, AND, THE, FEW, TIN, BIN}, use of foreign languages, letter schemes, and characters (e.g., Greek letters or Chinese characters), text of various colors and sizes, shift in font from normal to italics or bold-face or underlined, use of graphical ASCII characters such as those above the digits from 1-9 and 0 when using the shift key on a United States computer keyboard, i.e. {!, @, #, $, %, ^, &, (, )}. Other contemplated sets of elements that could be included in saccade cards include other font sets or icons indicating direction {➤⇩⇧⇨}, {<^>}, or emotion (e.g., emoticons as shown in FIG. 12B).

Figure 12C:
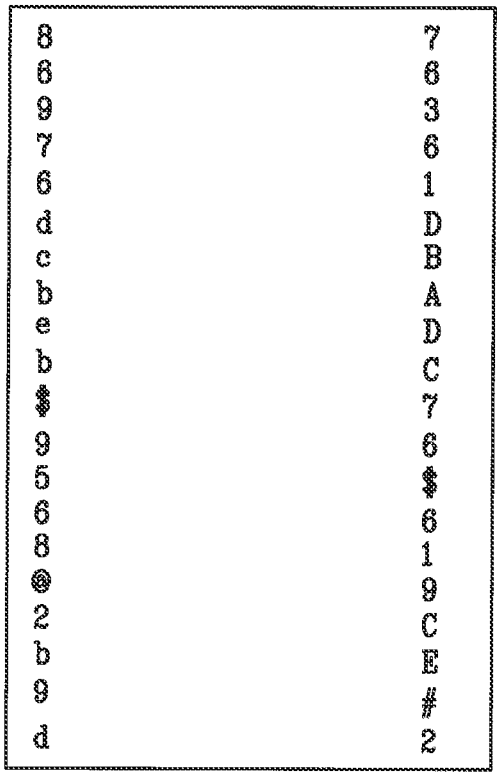
Figure 12D:
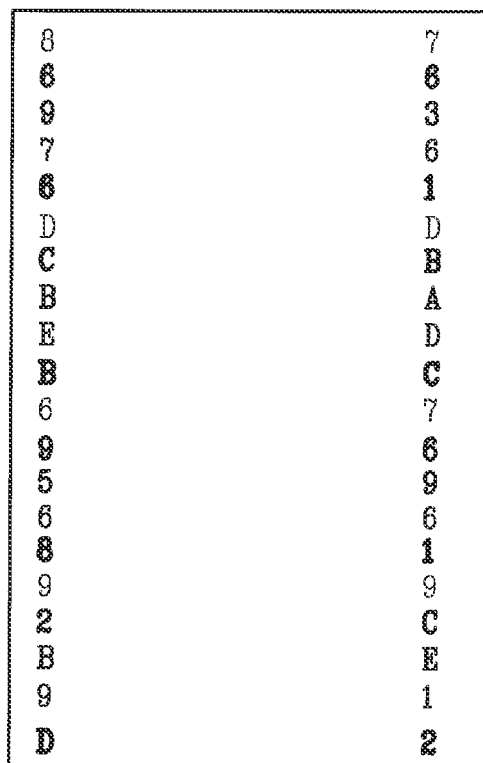

FIGS. 10A and 10B provide an alternate set of Card A and Card B vertical cards. Permutations of a given arrangement of elements are considered as part of the present invention as well. Consider what happens if one permutes in an orderly or stochastic fashion the elements from one card to another. Looking at the elements in the left column of FIG. 10B, if one shifts 1 to 3, 3 to 5, 5 to 7, 7 to 9 and 9 to 1 leaving the even elements alone, one would get the left column as shown in FIG. 10C (the right column remains unchanged). If one permutes the same elements as just listed in FIG. 10C in the left column but, in addition, randomly rather than systematically as just shown permutes all A to 2, 2 to B, B to D, then one would obtain another embodiment of the present invention, shown with the left column as permuted in FIG. 10D. Furthermore, FIGS. 11A, 11B, and 11C provide variants on the second style of mix element Card B, where the capital letters of FIG. 11A are permuted using arrows in FIG. 11B and individual element set shifts are incorporated in FIG. 11C. FIG. 12A includes both upper and lower case characters; FIG. 12B includes various smiley or sad faces; FIG. 12C includes various control characters like "@", "^", and "#"; in FIG. 12D, one can see the additional use of color amongst the elements of a given card. FIGS. 13A, 13B, and 13C illustrate horizontal cards with varying degrees of performance and set shift challenge. In addition, another particular embodiment of the present invention includes the use of repetitive elements as the lead element in the horizontal row position. This would make for a more challenging saccade whereby the subject would need to pay more particular attention to not make a mistake between leading elements in adjacent rows within the horizontal saccade cards.

Single Mode Assessment of a Subject Conducting a Saccade Task

The systems and methods of the invention comprise device and equipment form factors that can easily be positioned on or around the human body to both stimulate various senses as well as collect an eye tracking data as a bio-signal. In this case, presentation of saccade cards in various sequences can be used to create a health assessment task. This can include just eye movement alone or in conjunction with other biosensor data streams. And in particular, can be used for eye exam, learning disability and concussion related injury assessment. Furthermore, the system can be used for psychiatric and mental health evaluation and diagnosis by creating objective biomarkers.

The system and methods of the present invention include in various embodiments presentation of visual stimuli in the form of saccade cards while monitoring the response of the subject to the visual stimuli, in particular with an eye tracking device. The placement of a camera can determine the position of each or both eyes as a function of time $E\_i$ $(x,y,t)$, where $E\_i$ is the position of the ith eye (either left or right), $(x,y)$ is the spatial position measured of the subjects eye gaze by the eye tracker, and time t. The camera can be either a standard imaging sensor, such as a web-cam, or a specialized camera designed to track the position of the eye using the glint which appears on the white of the eye when light is shinned or strobed on the eye's curvilinear surface.

Multimodal Assessment of a Subject Conducting a Saccade Task

The systems and methods of the invention comprise device and equipment form factors that can easily be positioned on or around the human body to both stimulate various senses as well as to collect a multitude of bio-signals. In this case, presentation of saccade cards in various sequences can be used to create a health assessment task, including for the assessment of brain health and function.

The system and methods of the present invention include in various embodiments presentation of visual stimuli in the form of saccade cards while monitoring the response of the subject to the visual stimuli. Various bio-sensors can be arranged around the human subject to record various biological data streams to help characterize the health of the subject. In particular, an electro-encephalography (EEG) biosensor can non-invasively record the electrical activity of the brain using classical or novel brainwave biosensors. Moreover, the voice and auditory response of the subject can be recorded by the placement of a recording microphone in the vicinity of the subject when they are conducting the saccade card task. Furthermore, as in the above example, the placement of a camera can determine the position of each or both eyes as a function of time $E\_i(x,y,t)$, where $E\_i$ is the position of the ith eye (either left or right), $(x,y)$ is the spatial position measured of the subjects eye gaze by the eye tracker, and time t. The camera can be either a standard imaging sensor, such as a web-cam, or a specialized camera designed to track the position of the eye using the glint which appears on the white of the eye when light is shinned or strobed on the eye's curvilinear surface. Additional bio-sensors can be contemplated in such as a setup as well, including the temperature of the individual, the arterial oxygen level in the human subject, the heart rate of the subject (often measured using a pulse-oximetry sensor), the motion and dynamics of the position of the head as measured by a multi-axis (2 or 3-axis) accelerometer and gyrometer (2 or 3-axis for each) which will enable the correlation of accelerometer movement with the measurement of eye position by the external camera facing the individual's face. Additional non-limiting biosensors and measurements can also be contemplated which include galvanic skin conductance, proximity, geographic localization, and dual webcam, which would give additional information regarding the health and function of the subject under investigation and assessment. These could be combined with other biomarkers from other modalities to include genetic markers, epigenetic markers, blood based chemical analytes, peptides, and proteins, as well as cerebrospinal fluid (CSF) chemical analytes, peptides and proteins.

Use of the Multimodal System to Create Multimodal Signatures for Disease or Injury or Other Non-Traditional Use Using the system of the invention, one can acquire multiple streams of data during saccade tasks. From these multimodal biosensors data streams, one can conduct signal analysis on each stream and extract data features from the individual biosignals, or one can use one biosignal data stream A to gate or correlate biosignals from another data stream B. In this way, one can increase signal to noise ratio by selecting portions of signal B to based solely on data and features observed on measured in biosignal A.

In one particular embodiment, a subject can be asked to rotate their head left to right and back again as if indicating "no" several times. This lateral rotation from ear to ear can be measured by an accelerometer placed into a head piece that records the electrical activity of the brain. At the same time and with millisecond or better precision, a webcam or external camera can record the position of the eye. With careful analysis, one can correlate the head motion with the eye gaze. Where there is synchronous motion between the two (e.g. the plot of head rotation on the x-axis and eye gaze on the y-axis) is smooth and continuous, then this would be evidence of a well-coordinated head rotation and eye gaze.

If the same plot for a different subject were discontinuous or chaotic in nature, this would evidence for abnormal head rotation and gaze, thereby signaling a need for further evaluation.

Use of Correlation Analysis Across Time Series in the Multimodal Biosignal Data Streams The present invention explicitly contemplates the use of two point, three point or higher order correlations, coherence and other multi-variate calculated measurements in space and time to examine interactions between the various biosensor data streams. For instance, one could look at the time series of samples from a microphone sampled at 8 KHz and the EEG from a single lead sensor sampled at 512 Hz and look at any of the various correlation functions available in the literature. In addition, techniques such as spatial coherence and concordance can be used either between two sensors of the same modality (which is typically done for EEG) but similar approaches can be adapted to the multiple streams of biosignal data from the system of the present invention.

As CPU processing power increases into smaller form factors, one can envision the real-time processing of multiple biological signal data streams through embedded DSP and other high end MCU devices embedded within the head REM or trunk located REM or extremity located REM modules.

Use of an Infra-Red Eye Tracker During Neuro-Opthalmologic Tasks

As an alternate approach to a classic eye tracker, the Google Glass device could be employed as an elementary eye tracker. In addition, one could employ other dedicated hardware such as from Tobii or other manufactures and stream left and right eye position and pupil diameter measurements continuously. From the output eye gaze position, one can make measurements of fixation on various objects in a stimuli field of view, as well as saccades or anti-saccades which are of interest. Stimulation visuals could include instructions, static photographs or artistic creations, movies, web pages, advertisements, pdf documents, etc. Predefined areas of interest (AOI) can be created and the eye gaze data superimposed on top of the areas of interest to define metrics of fixation and saccade relative to the AOI's. Candidate metrics can be extracted from the eye gaze data to include time to first fixation, fixation duration, total fixation duration, visit duration, total visit duration, percentage fixated, saccade accuracy, anti-saccade accuracy. These extracted features can then be incorporated into summary feature tables of the present invention and used to construct multi-variate signatures and classifiers along the with extracted brainwave features, speech recognition features, neuropsychological test data, accelerometer based balance measures, etc.

Use of Electrooculography During Neuro-Opthalmologic Tasks

As an additional alternative approach to a classic eye tracker, measuring the corneo-retinal standing potential that exists between the front and the back of the human eye may be used to calculate the position of the eye. Illumination of the retina generates an electrical potential by stimulation of specialized type of tissue containing photoreceptors. One can make differentially amplified measurements of the electrical potential generated across the orbit, eye cavity, to calculate the retinal position and by corollary, movement, saccades, and the fixation point within a field of view. Viewing position may be overlaid on AOI's as with above described eye tracking methods. Candidate metrics can be extracted from the eye gaze data to include time to first fixation, fixation duration, total fixation duration, visit duration, total visit duration, percentage fixated, saccade accuracy, and/or anti-saccade accuracy. These extracted features can then be incorporated into summary feature tables of the present invention and used to construct multi-variate signatures and classifiers along the with extracted brainwave features, speech recognition features, neuropsychological test data, accelerometer based balance measures, etc.

Use of Other "Eye Gaze" or "Eye Tracking" Means Including Web Camera and Other Approaches As an additional alternative approach to a classic eye tracker, measuring the position of the eye by an optical image and online or off-line digital or analog image processing is contemplated. As a non-limiting embodiment, an inexpensive web camera is useful as a primary sensor to collect images of the eye gaze of a subject for subsequent image processing and eye tracking determination, and is an embodiment of the invention. As a subject reads off elements from the display, whether paper, computer or other display device, the position of the eye can be measured in any number of equivalent ways, giving a relative or absolute position of the eye, independently or as an average of both eyes, to create features as objective biomarkers useful for any number of means. It should be appreciated by one skilled in the art that alternate methods can be employed and that slower means are not necessarily better or worse, just different than faster sampling rate techniques.

EXAMPLES

While the above description contains many specifics, these specifics should not be construed as limitations on the scope of the invention, but merely as exemplifications of the disclosed embodiments. Those skilled in the art will envision many other possible variations that are within the scope of the invention. The following examples will be helpful to enable one skilled in the art to make, use, and practice the invention.

Example 1. Internal Company Cross-Validation of the Results Between Peer-Reviewed Published Saccade Tasks and the Novel Saccade Task of the Present Invention Internal research was conducted on healthy normal subjects comparing their performance on the King-Devick saccade cards (two passes through the three cards) and the novel saccade cards as illustrated in FIGS. 4, 5, 6 and 7. Healthy normal subjects were asked to sit down before a desktop computer and read-off the various saccade cards from left to right, top to bottom as fast as possible without errors. The peer reviewed published K-D test scores are plotted on the x-axis and the novel saccade scores are plotted on the y-axis for the same individual human subjects. Data were collected with stop watch as defined in the peer-reviewed literature for both tasks.

Data tables were created with each human subject as an individual row and the individual card times for the 6 cards listed for the K-D test, the overall K-D time to complete three cards with minimal errors as compared to the various times measured for each of the 4 novel saccade cards as illustrated in FIGS. 5 and 6. Scatter plots were constructed and goodness of linear fits determined between the literature supported K-D saccade cards and the novel saccade cards of the present invention.

The total time for the King-Devick test was calculated according to the published procedure of using the minimal number of errors and then summing the individual times to read all three cards in succession. The outcome variables for the novel saccade cards of the present invention were determined as described above, following the scheme outlined in the Development Eye Movement literature. All analysis was conducted in JMP Pro v10 from SAS (Cary, N.C.).

Figure 14A:
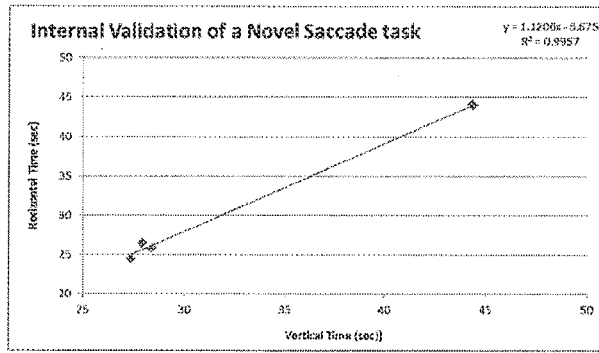
FIG. 14A is a graph of Vertical Time versus Horizontal time showing a strong correlation between the two times.
Figure 14B:
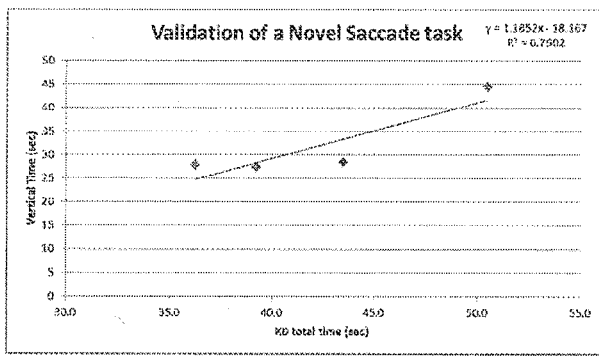
FIG. 14B is a graph cross validating the novel saccade card Vertical Time as a function of a published metric, the K-D test total time.
Figure 14C:
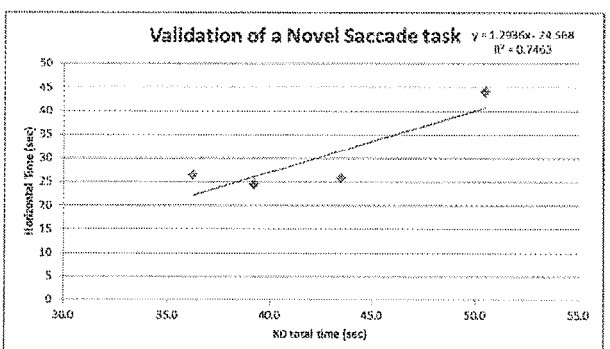
FIG. 14C is a graph cross validating the novel saccade card Horizontal Time as a function of a published metric, the K-D test total time.
Figure 14D:
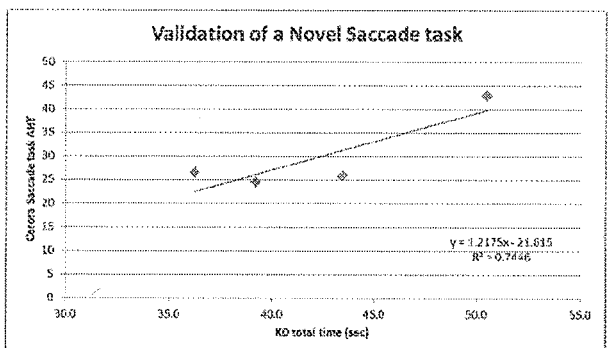
FIG. 14D is a graph cross validating the novel saccade card Adjusted Horizontal Time as a function of a published metric, the K-D test total time.

As can be seen in FIG. 14, the internal validation of the novel saccade cards is shown in the top figure comparing the vertical time and the horizontal time, FIG. 14A. The correlation coefficient is excellent with $R^2=0.9957$ for N=4 subjects. In addition, comparison of K-D test time to Vertical Time (FIG. 14B) looks very promising with $R^2=0.79$. In FIG. 14C, the Horizontal time is calculated with good $R^2=0.7463$ for N=4 subjects. Lastly, the Adjusted Horizontal Time is plotted a function of K-D Test time in FIG. 14D, showing good $R^2=0.7446$ for N=4 subjects.

Example 2. Head Rotation with Eye Gaze Movement Study (Prophetic Example)

One means to assess the health of a patient is to utilize an accelerometer on the head to measure rotational motion and use the eye tracker to see if while the head is rotating whether the eyes are able to dynamically balance and remain fixed on a single spot in space. This tests the hypothesis that a healthy brain can keep the spot fixed while the head rotates, while the unhealthy brain is not able to maintain fixation and moves chaotically or irregularly during such a trial. This could be accomplished by three to five left to right, right to left rotations as if saying "no". The input is the accelerometer data characterizing the head motion while the outcome variable is the eye position and whether there is fixation or not.

Example 3. Tobii X2-30 Compact Eye Tracker Implementation

Figure 15:
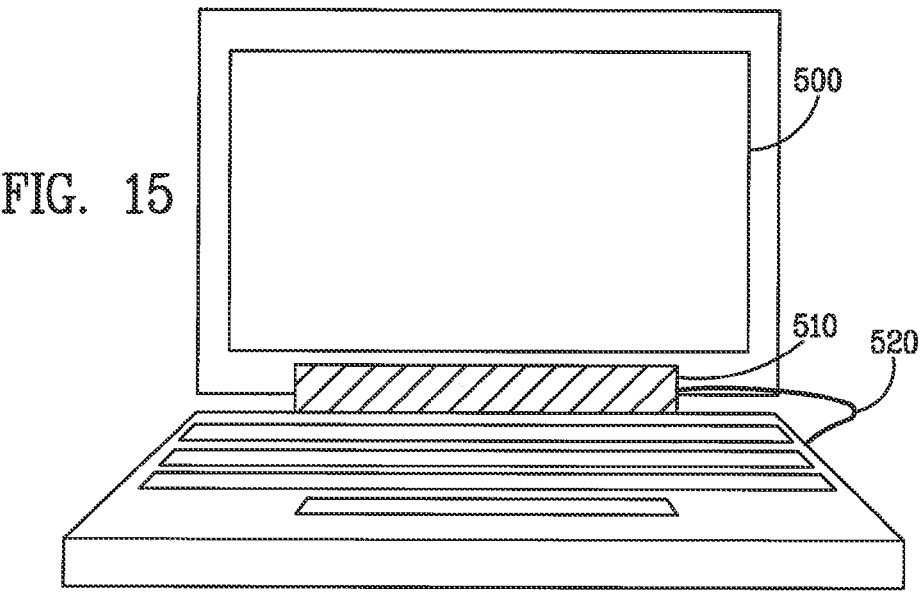
FIG. 15 illustrates a schematic of a laptop PC screen including a compact eye tracker used to acquire eye tracking data in an exemplary embodiment.
Figure 16:
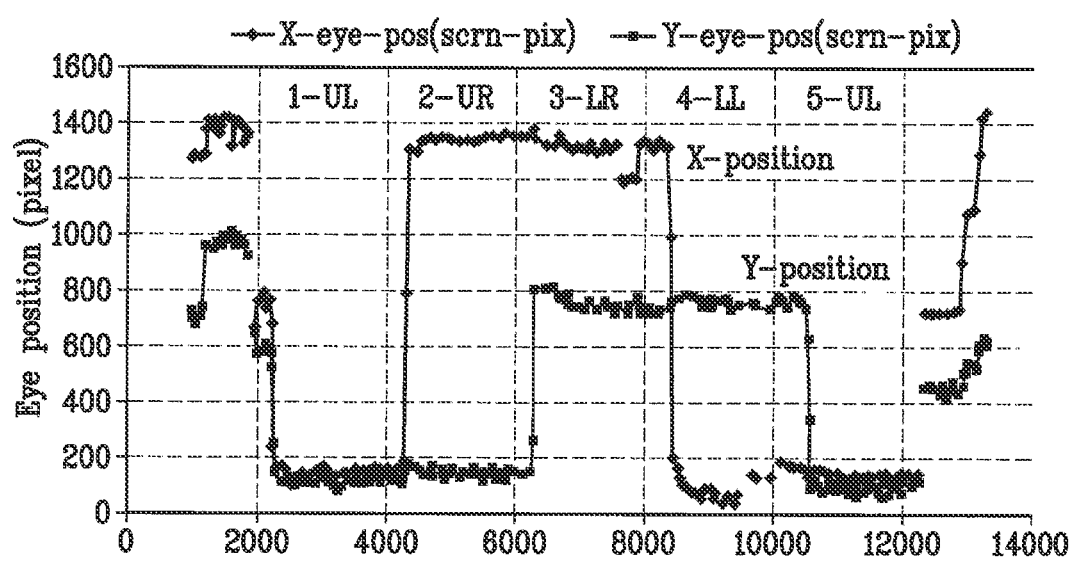
FIG. 16 illustrates a plot of eye position for both eyes averaged.

The inventors successfully incorporated a Tobii X2-30 Compact eye tracker into the data acquisition paradigm as eye tracking means in accordance with the invention. FIG. 15 shows a schematic of a laptop PC 500 screen but it could equally work for a tablet or smartphone form factor. The eye tracker 510 is plugged into a USB port 520 in the present wired mode, but WiFi or other wireless is contemplated as well. First, stimuli were created to check the analytical performance of the eye tracker to extreme conditions. Numbers were placed on slides in the corners of the screen and shown for 2 second intervals before moving onto the next corner in a clockwise rotation. Eye position was plotted for both eyes averaged as shown in FIG. 16. The output of the eye tracker very nicely produced the expected trace with the 16:9 aspect ratio apparent in the asymmetric x position and y position.

In a follow-up experiment, neuro ophthalmologic saccade cards (King Devick test) were presented while recording EEG brainwaves, the microphone and the forward facing webcam on a laptop. Heat map representations of where the eye gaze was concentrated relative to the stimulation numbers on the various cards was measured. The use of various predefined Areas of Interest AOI) to enable measurements of eye gaze that intersect with the AOIs to define time durations, fixations, and saccade accuracy to track the targets of interest. One can investigate if there is the appearance of significant eye gaze off target at the beginning of a row relative to the end of the same row.

Example 4. Multimodal Implementation (Prophetic Example

One means to assess the health of a patient is to utilize a multimodal biosensor system that includes (1) an EEG brainwave sensor, (2) an accelerometer and gyrometer pair on the head to measure both linear and rotational motion, (3) a microphone to record the voice of the subject, and (4) the use of an eye tracker to measure the position and movement of the eyes either individually or in unison. In addition, one could envision the incorporation of galvanic skin conductance biosensor measurements (typically associated with emotional response due to sweat production), pulse-oximetry measurements of arterial oxygen and heart rate (including heart rate variability), as well as other neuropsychological and biosensor based modalities. Thus, if a subject is presented sensory stimulation such as a series of saccade cards of the present invention, then in one task one could simultaneously measure the brainwaves, head motion, eye position, voice, heart rate, arterial oxygen, and sweat related properties of the test subject while conducting the single task. In another case, the visual stimulation could be a series of images, sounds and smells associated with a condition designed to evoke a response from various valences, using such as the well calibrated tools as the NIH International Affective Pictures System (TAPS) or the International Affective Digital Sounds (TADS) at the University of Florida or equivalent sets yet to be developed and characterized. This would be useful in the assessment of warfighters for anxiety disorders like Post-Traumatic Stress Disorder, a common comorbidity with traumatic brain injury seen in warfighters post conflict.

Those skilled in the art will also appreciate that the invention may be applied to other applications and may be modified without departing from the scope of the invention. For example, the other combinations of biosensor signals and saccade cards can be employed on a server, in the cloud, in the electronics module, or on a local PC, tablet PC, smartphone, or custom hand held device. The recording of the biosensor data may be automated or may be manual, such as by measuring the saccade test results using a stopwatch. Accordingly, the scope of the invention is not intended to be limited to the exemplary embodiments described above, but only by the appended claims.

What is claimed:
1. A system for capturing biological sensor data for assessing brain health of a subject, comprising:
    a plurality of biological stimulation devices that simultaneously record biological sensor data from the subject in response to biological stimulation, said biological stimulation devices including an eye saccade test that measures saccadic performance and ocular motility of the subject, the eye saccade test including at least one saccade card that includes first and second sets of differentiated elements for readout by the subject during a saccade task, the first and second sets of differentiated elements being spaced on the at least one saccade card such that the subject must shift between the first and second sets of differentiated elements during readout of the first and second sets of differentiated elements during the saccade task;
    a recording device that records as an objective biomarker of the brain health of the subject at least one of the subject's eye positions and the subject's voice and auditory responses at different points in time in response to the eye saccade test; and a processing device that processes the biological sensor data from the subject in response to biological stimulation to assess the brain health of the subject, the biological sensor data including recordings of at least one of the subject's eye positions and the subject's voice and auditory responses at different points in time.

2. A system as in claim 1, wherein the eye saccade test includes at least one saccade card that has at least one set of numerical elements and at least one set of non-numerical elements.

3. A system as in claim 1, wherein the first and second sets of differentiated elements are selected from at least two of the following: single digit numbers from zero to nine {0, 1, 2, 3, 4, 5, 6, 7, 8, 9}, the first six capital letters of the alphabet {A, B, C, D, E, F}, 2 digit numbers, 3 or more digit numbers, upper case letters of the alphabet {A, B, C, D, E, F, G, H, I, J, K, L, M, N, O, P, Q, R, S, T, U, V, W, X, Y, Z}, lower case letters of the alphabet {a, b, c, d, e, f, g, h, i, j, k, l, m, n, o, p, q, r, s, t, u, v, w, x, y, z}, two letter words with either uniform case or mixed case, three letter words with either mixed case or uniform case, foreign language characters, letter schemes, text of various colors and sizes, shift in font from normal to italics or bold-face or underlined, graphical ASCII characters above the digits from the group comprising: !, @, #, $, %, ^, &, *, and (,), and icons indicating direction or emotion.

4. A system as in claim 1, wherein said at least one eye saccade card includes a first saccade eye card including a column of vertical elements from the first and/or second set of elements in a first order from top to bottom on the first saccade eye card and a second saccade eye card including a row of horizontal elements corresponding to the elements in said column of vertical elements on said first saccade card except that the horizontal elements are disposed in the first order from left to right on the second saccade eye card.

5. A system as in claim 1, wherein said biological sensors include an eye tracking device that monitors the response of the subject in response to the presentation of at least one eye saccade card to visually stimulate the subject.

6. A system as in claim 5, wherein said eye tracking device includes a device that monitors the eye position and response of the subject in response to the presentation of said at least one eye saccade card to the subject.

7. A system as in claim 6, wherein said device includes an electrical potential measuring device that measures an electrical potential generated across an orbit eye cavity or a web camera that determines retinal position.

8. A method for assessing brain health of a subject, comprising:
measuring saccadic performance and ocular motility of the subject by presenting an eye saccade test to the subject, the eye saccade test including at least one saccade card that includes first and second sets of differentiated elements for readout by the subject during a saccade task, the first and second sets of differentiated elements being spaced on the at least one saccade card such that the subject must shift between the first and second sets of differentiated elements during readout of the first and second sets of differentiated elements during the saccade task;

recording as an objective biomarker of the brain health of the subject at least one of the subject's eye positions and the subject's voice and auditory responses at different points in time by manually noting time and accuracy of the subject's response or by using a plurality of recording devices in response to said eye saccade test; and processing recordings of at least one of the subject's eye positions and the subject's voice and auditory responses at different points in time to determine saccadic performance and ocular motility as an assessment of the brain health of the subject.

9. A method as in claim 8, further comprising repeating said measuring, recording, and processing steps to identify changes in said saccadic performance and ocular motility over time.

10. A method as in claim 9, further comprising correlating said identified changes in said saccadic performance and ocular motility over time to a brain health condition of the subject.

11. A method as in claim 10, further comprising using the identified changes in said saccadic performance and ocular motility over time to construct a multi-variate signature of the brain health condition of the subject.

12. A method as in claim 8, wherein recording biological sensor data from the subject includes tracking eye movement of the subject during presentation of at least one saccade card to the subject and monitoring a response of the subject in response to the presentation of said at least one eye saccade card.

13. A method as in claim 12, wherein said eye movement tracking includes using an electrical potential measuring device to measure an electrical potential generated across an orbit eye cavity or a web camera to determine retinal position during a saccade test.

14. A device as in claim 1, wherein said recording device comprises at least two of an electro-encephalography biosensor, a microphone, a camera, a temperature biosensor, an arterial oxygen biosensor, a heart rate biosensor, an accelerometer and gyrometer, and a galvanic skin conductance biosensor.

15. A method as in claim 8, wherein the first and second sets of differentiated elements are selected from at least two of the following: single digit numbers from zero to nine {0, 1, 2, 3, 4, 5, 6, 7, 8, 9}, the first six capital letters of the alphabet {A, B, C, D, E, F}, 2 digit numbers, 3 or more digit numbers, upper case letters of the alphabet {A, B, C, D, E, F, G, H, I, J, K, L, M, N, O, P, Q, R, S, T, U, V, W, X, Y, Z}, lower case letters of the alphabet {a, b, c, d, e, f, g, h, i, j, k, l, m, n, o, p, q, r, s, t, u, v, w, x, y, z}, two letter words with either uniform case or mixed case, three letter words with either mixed case or uniform case, foreign language characters, letter schemes, text of various colors and sizes, shift in font from normal to italics or bold-face or underlined, graphical ASCII characters above the digits from the group comprising: !, @, #, $, %, ^, &, *, and (,), and icons indicating direction or emotion.

* * * * *